United States Patent [19]

Scrivens

[11] 4,027,665
[45] June 7, 1977

[54] CARDIOVASCULAR DRAPE

[75] Inventor: George W. Scrivens, Edison, N.J.

[73] Assignee: Johnson & Johnson, New Brunswick, N.J.

[22] Filed: Mar. 3, 1976

[21] Appl. No.: 663,900

[52] U.S. Cl. .......................................... 128/132 D
[51] Int. Cl.² ...................................... A61B 19/06
[58] Field of Search ....... 128/132 D, 348, DIG. 26, 128/292

[56] References Cited
UNITED STATES PATENTS

| | | | |
|---|---|---|---|
| 1,724,443 | 8/1929 | Wheeler | 128/132 D |
| 3,537,446 | 11/1970 | Rowland et al. | 128/132 D |
| 3,561,440 | 2/1971 | Bayer et al. | 128/132 D |
| 3,721,234 | 3/1973 | Hadtke et al. | 128/132 D |
| 3,799,161 | 3/1974 | Collins | 128/132 D |
| 3,856,006 | 12/1974 | Krzewinski | 128/132 D |
| 3,881,474 | 5/1975 | Krzewiski | 128/132 D |
| 3,889,667 | 6/1975 | Collins | 128/132 D |

Primary Examiner—Lawrence W. Trapp

[57] ABSTRACT

A surgical drape particularly suitable for cardiovascular surgery comprising a main sheet, preferably T-shaped in configuration, of flexible drapable material and at least two fenestrations covered by closure members which carry a pressure sensitive adhesive on their lower surfaces. The drape also includes improved means for securing thin, flexible elements such as suction tubing and electrical wires to the upper surface of the drape. The drape is folded longitudinally and transversely into a compact unit which may be packaged and thereafter sterilized in its packaged condition. The folded drape may be easily and quickly unfolded and applied to the patient in an aseptic manner.

32 Claims, 30 Drawing Figures

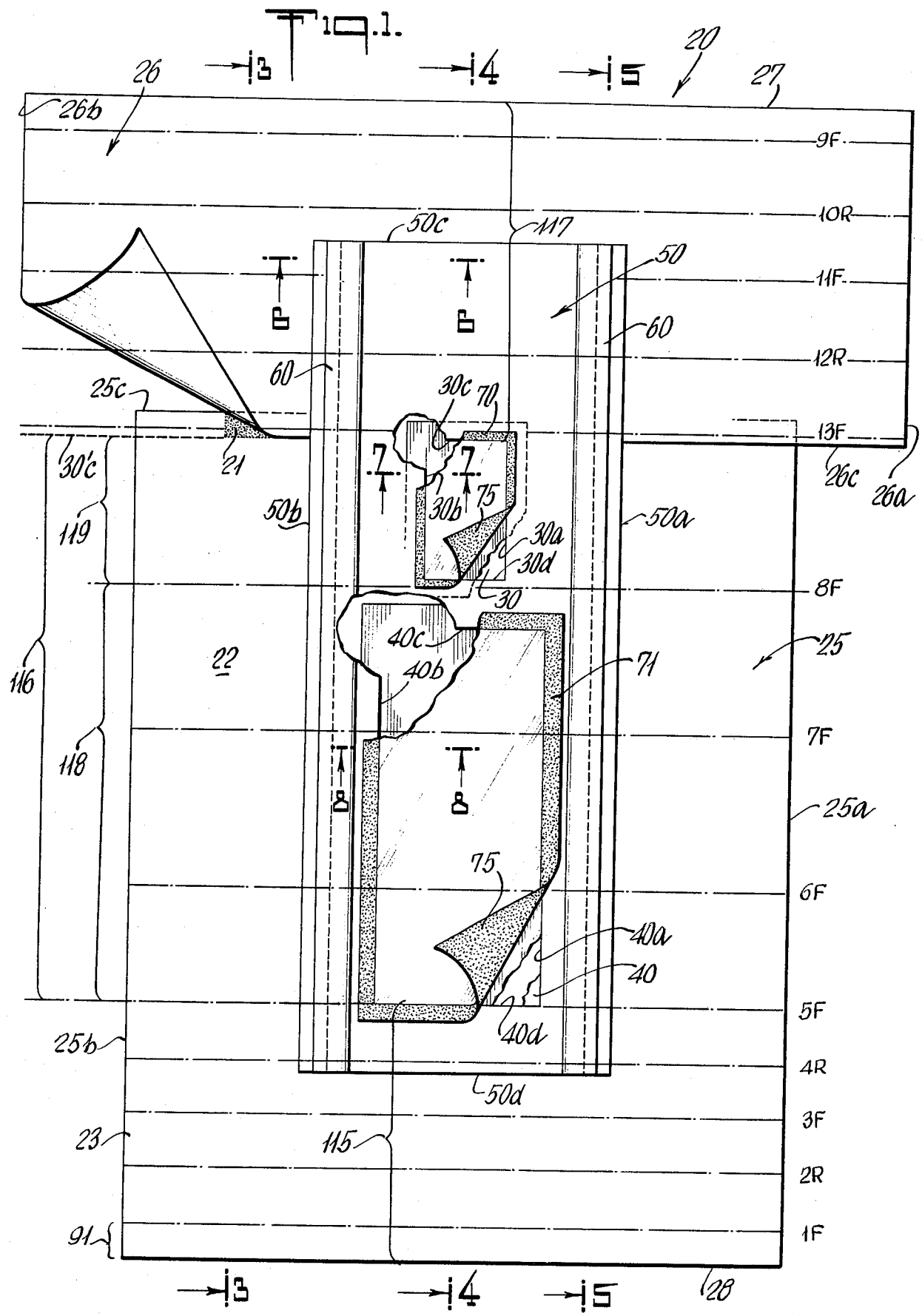

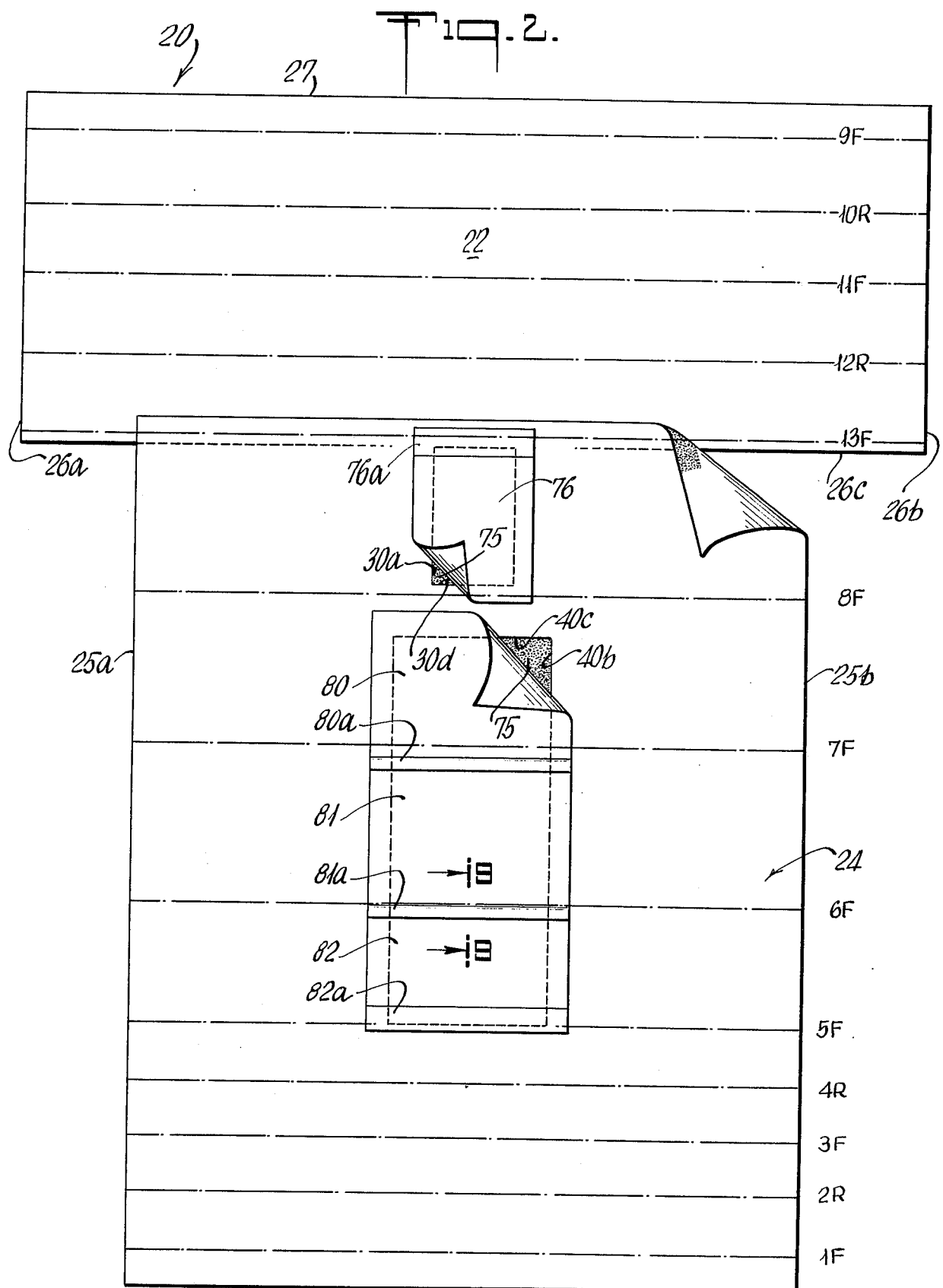

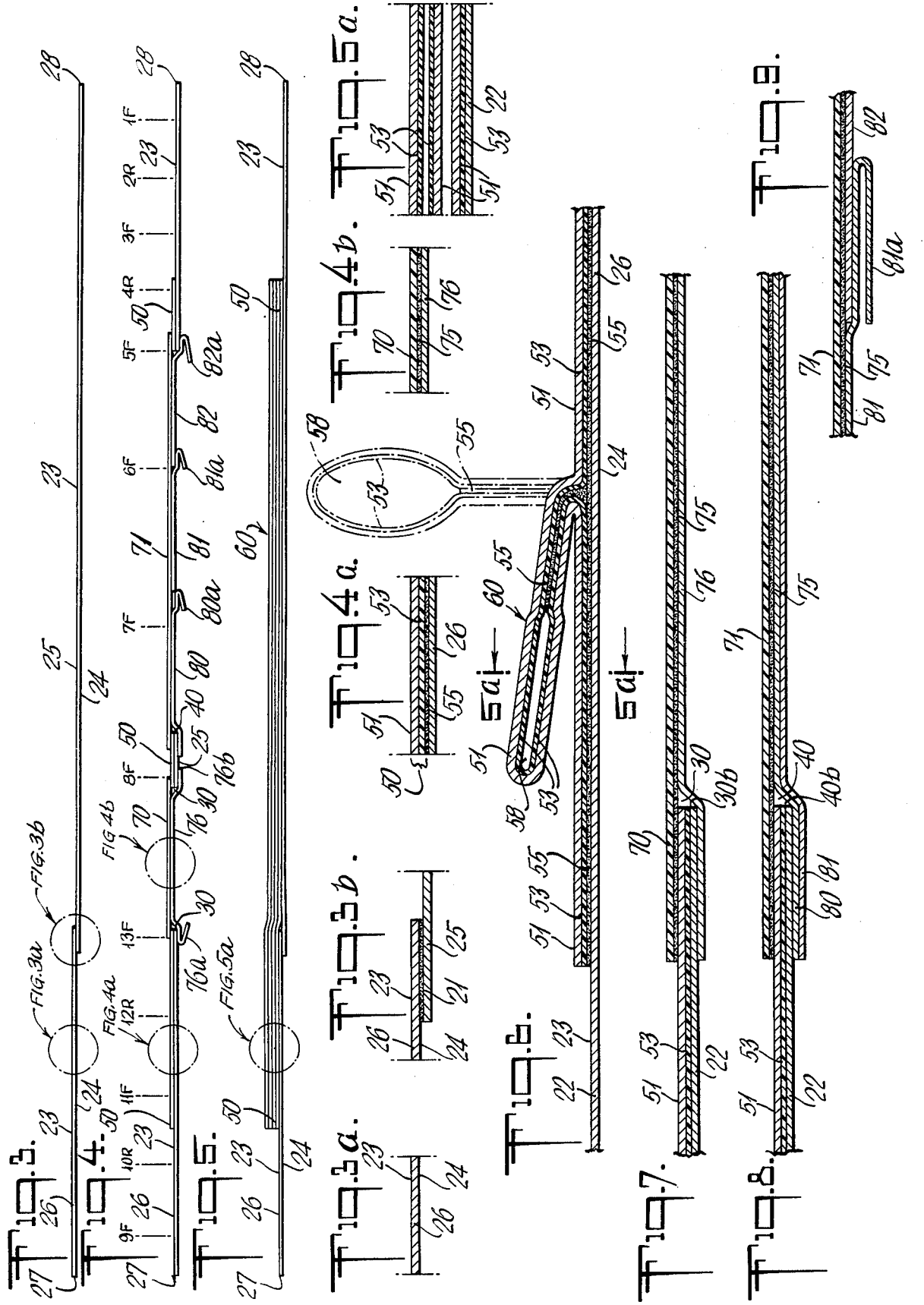

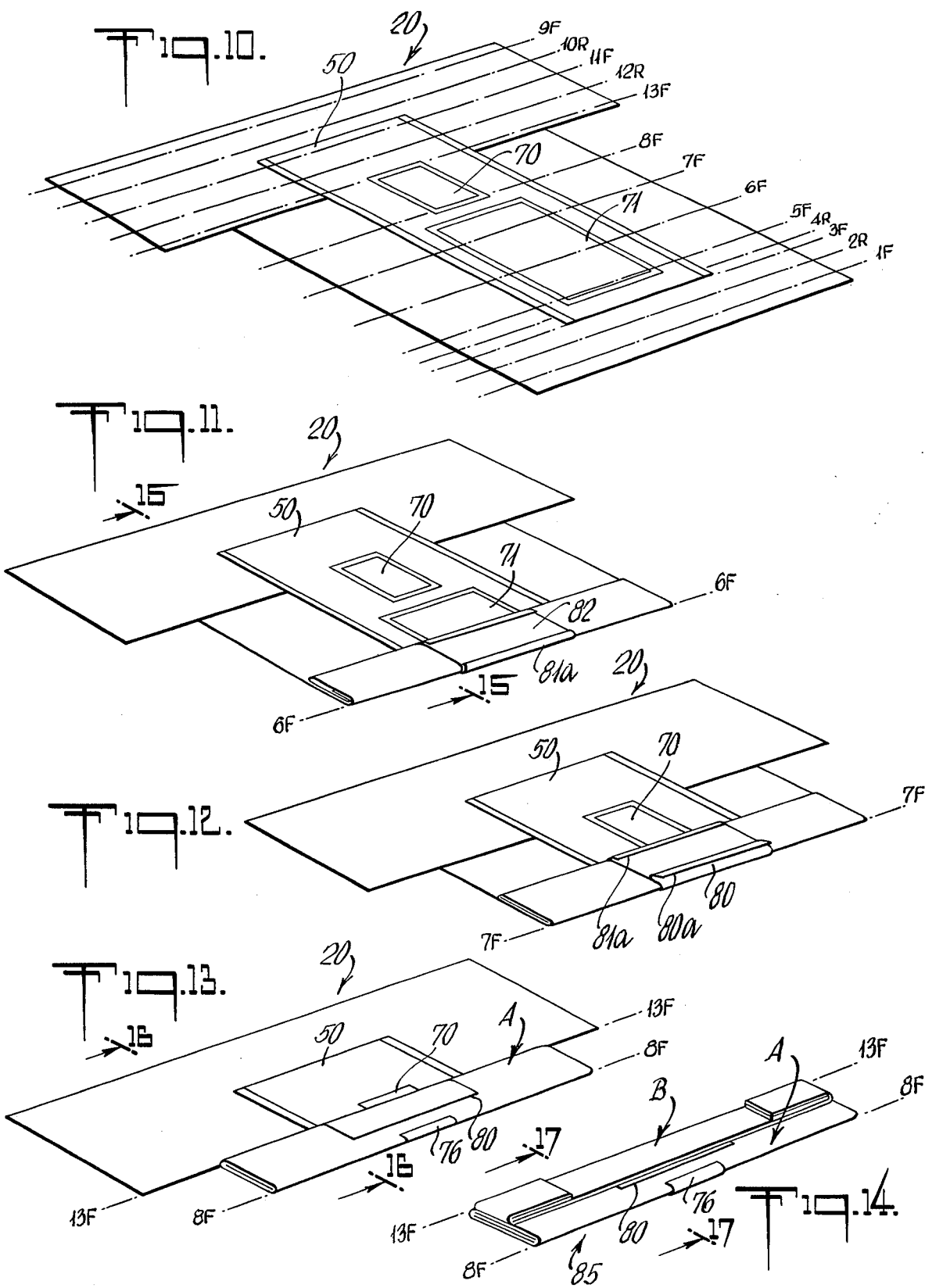

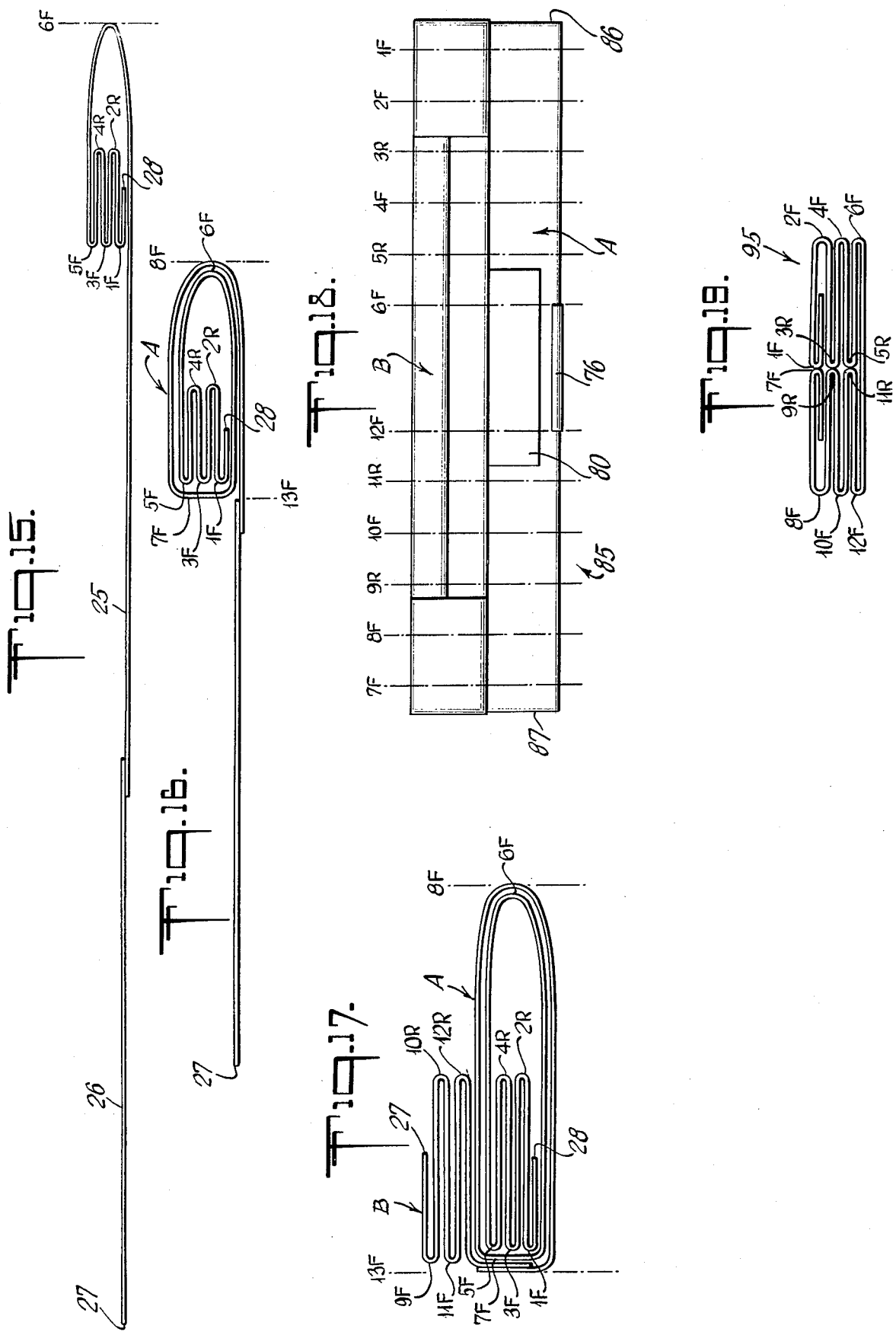

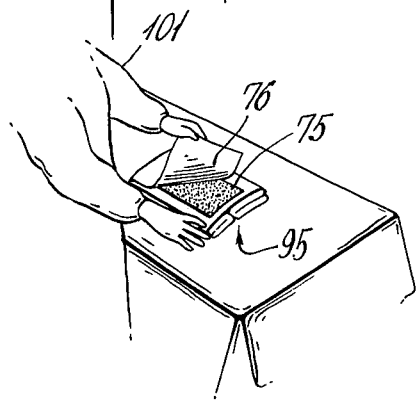
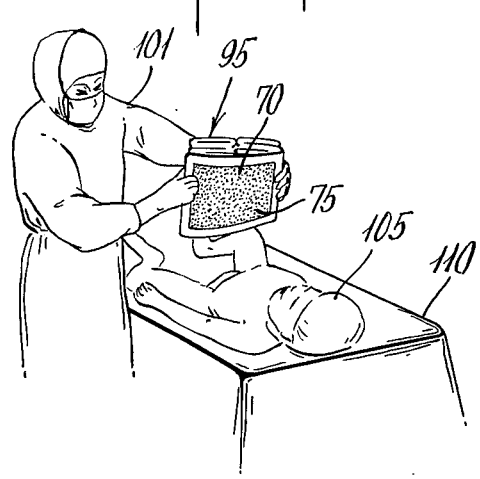
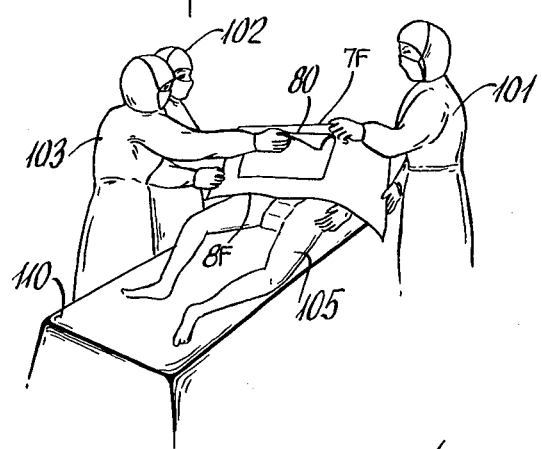
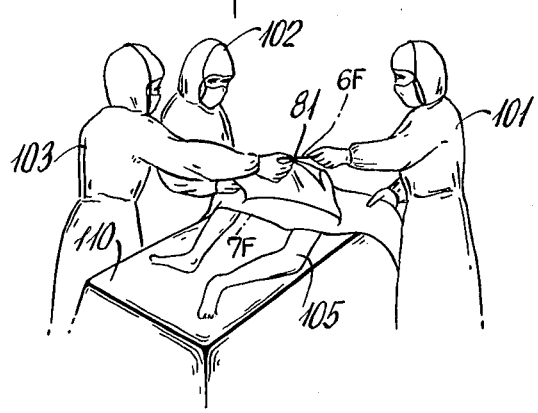
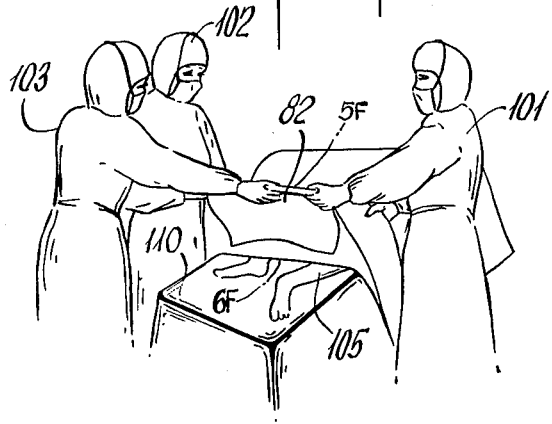
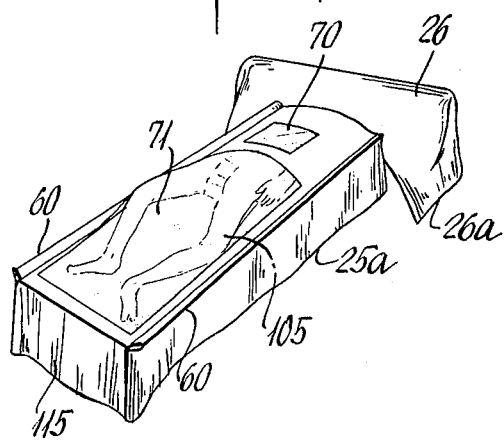

CARDIOVASCULAR DRAPE

BACKGROUND OF THE INVENTION

1. Field of the Invention

This invention relates to surgical drapes and the like, and more particularly to disposable surgical drapes which are especially useful in cardiovascular surgery.

2. Description of the Prior Art

The prior art has provided a variety of drapes, both reusable and disposable, which are used to cover the body of a patient during a surgical or related procedure and which serve to maintain a sterile barrier around the operative site. In some cases, there is available a single surgical drape which is suitable for a given surgical procedure, while in other cases it is necessary to apply two or more surgical drapes to a patient in order to properly prepare him for surgery. For example, in the case of cardiovascular surgery, where it is necessary to expose one or both legs of the patient in addition to the chest area, it has been proposed to use one fenestrated drape for the chest area and a second fenestrated drape for covering the area of the body from roughly the waist to the feet. The use of two or more drapes in a given surgical procedure makes it necessary for the hospital to maintain a stock of different drapes. The use of two drapes consumes valuable time of operating room personnel and also requires that the drapes be clipped together by, for example, towel clips. Quite disadvantageously, such clipping tends to put holes in the drapes which holes may provide sites for migration of bacteria.

SUMMARY OF THE INVENTION

A principal feature of the present invention is the provision of a surgical drape that is particularly useful in cardiovascular surgery.

The drape of the present invention comprises a flexible main sheet having an upper and a lower surface, the lower surface being that surface which will come into contact with the patient's body and the upper surface being that surface which will face away from the patient's body while the drape is in use. The main sheet has at least two fenestrations therein. The first of these fenestrations is generally rectangular in shape and is so located in the main sheet, that when the drape is placed on the patient, it will overlie the general region of the patient's chest. The second fenestration is also generally rectangular in shape but is wider and more elongated in configuration than the first fenestration. The second fenestration is so placed in the main sheet that, when the drape is placed on the patient, this fenestration will overlie that portion of the patient's body extending roughly from the lower abdomen area down to the ankle area.

Each of the fenestrations in the drape is covered by a closure member comprising a relatively thin film of thermoplastic organic polymer. The films covering the fenestrations should be flexible and drapable and should be capable of being sterilized without being deleteriously affected. The lower surface of each closure member is coated, in the area lying within the periphery of the fenestration which it covers, with a pressure sensitive adhesive which will withstand sterilization and adhere to the skin of a patient. The pressure sensitive adhesive coating on each of the closure members is protected, prior to use, by one or more removably adherable release sheets.

Another feature of the drape of the present invention is the provision of reinforcing material around the areas of the main sheet adjacent the fenestrations. This reinforcing material provides extra strength and abrasion resistance in those regions of the drape adjacent the operative sites.

Still another feature of the drape is the provision of improved means by which various operating room accessories such as suction tubing, electrical lead wires and the like may be secured in desired position on the upper surface of the drape.

In accordance with another aspect of the present invention there is provided a folded cardiovascular drape which can be easily and aseptically applied to the patient. The folding is such that the size of the drape in its spreadout, in use configuration (which size may approach 11 feet if it is desired to have the drape cover the anesthesia screen, the patient, and the lower end of the operating table) is greatly reduced, thus making it much more convenient for the manufacturer to package and for hospital personnel to store and handle. More importantly, as will be seen, the drape is so folded that it can be applied to the patient in distinct stages. This is particularly important where, as is the case here, the fenestrations are covered with film which carries pressure sensitive adhesive. In this instance, due care must be taken to insure that the area of pressure sensitive adhesive exposed at any one time is not so large that it becomes difficult or impossible to properly apply the drape. Care must also be exercised to prevent the inadvertent contact of a portion of the adhesive coated cover sheet with another surface of the drape thus rendering the drape useless.

BRIEF DESCRIPTION OF THE DRAWINGS

The invention will be better understood upon reading the following detailed description and upon reference to the appended drawings, in which:

FIG. 1 is a top plan view of a surgical drape in accordance with the present invention, with some parts having been cut away and other parts having been turned back for purposes of illustration;

FIG. 2 is a bottom plan view of the surgical drape of FIG. 1, with some parts turned back for purposes of illustration;

FIG. 3 is a schematic cross-section taken along line 3—3 of FIG. 1;

FIG. 3a is a magnified view of the circled portion at the left hand side of FIG. 3;

FIG. 3b is a magnified view of the circled portion toward the right hand side of FIG. 3;

FIG. 4 is a schematic cross-section taken along line 4—4 of FIG. 1;

FIG. 4a is a magnified view of the circled portion at the left hand side of FIG. 4;

FIG. 4b is a magnified view of the circled portion toward the right hand side of FIG. 4;

FIG. 5 is a schematic cross-section taken along line 5—5 of FIG. 1;

FIG. 5a is a magnified view of the circled portion of FIG. 5, and is also a sectional view taken along line 5a—5a of FIG. 6;

FIG. 6 is a greatly enlarged cross-sectional view taken along line 6—6 of FIG. 1;

FIG. 7 is a greatly enlarged cross-sectional view taken along line 7—7 of FIG. 1;

FIG. 8 is a greatly enlarged cross-sectional view taken along line 8—8 of FIG. 1;

FIG. 9 is an enlarged cross-sectional view taken along line 9—9 of FIG. 2;

FIG. 10 is a perspective view of the drape of FIG. 1 with the fold lines for the longitudinal folding being shown in dot and dash;

FIG. 11–14 are perspective views showing the drape of FIG. 1 in various stages of folding;

FIG. 15 is an enlarged schematic cross-section taken along line 15—15 of FIG. 11;

FIG. 16 is an enlarged schematic cross-section taken along line 16—16 of FIG. 13;

FIG. 17 is an enlarged schematic cross-section taken along line 17—17 of FIG. 14;

FIG. 18 is a top plan view of the drape after it has been longitudinally folded and showing the fold lines for the transverse folding;

FIG. 19 is a schematic cross-section of the drape in its transversely folded configuration; and FIGS. 20–25 illustrate the procedure for applying the folded drape to a patient.

DESCRIPTION OF THE PREFERRED EMBODIMENT

Referring now to the drawings, wherein like referenced characters designate like or corresponding parts throughout the several views, there is shown a preferred embodiment of a surgical drape in accordance with the present invention. This drape is particularly well suited for use in cardiovascular surgery. Surgical drape 20 is generally T-shaped in configuration and comprises a main sheet 22 of flexible drapable material; A first fenestration 30 through which the surgeon will perform some portions of the surgical procedure; a second fenestration 40 through which the surgeon will perform other portions of the surgical procedure; a reinforcing panel 50, and means 60 by which auxiliary surgical equipment, such as electrical wires, suction tubing and the like may be securely retained on the drape in a position adjacent one or both fenestrations. Inasmuch as first fenestration 30 is designed, as will be seen, for placement over and adherence to the chest area of a patient about to undergo surgery, it is sometimes referred to herein as the "chest fenestration". Similarly, since fenestration 40 is designed for placement over and adherence to one or both legs of the patient, it is sometimes referred to herein as the leg fenestration.

Main sheet 22, which may comprise any flexible, drapable woven, nonwoven, or plastic material, has an upper surface 23 and a lower surface 24. It will be understood that, in the surgical drape under discussion, lower surface 24 (the surface viewed in FIG. 2) will contact the patient when the drape is in use, while upper surface 23 (the surface viewed in FIG. 1) will face away from the patient. Main sheet 22 comprises a generally elongated lower or body portion 25 and a transversely disposed upper or cross-arm portion 26, the transversely extended portions of which may be used to cover the patient's arms during surgery. Body portion 25 has a pair of opposed side edges 25a and 25b; and cross-arm portion 26 has a pair of opposed side edges designated 26a and 26b. Cross-arm portion 26 has a top edge 27 corresponding to the top edge of the drape, and a bottom edge 26c. Body portion 25 has a top edge 25c and a bottom edge 28 corresponding to the bottom edge of the drape. Preferably main sheet 22 comprises a nonwoven fabric treated to make it repellent to liquids such as water, alcohol, wound exudate, saline and the like which are likely to be used or encountered during surgery. It will be understood that main sheet 22 may be cut from a single T-shaped piece of material if so desired; such T-shaped piece of material can be slit at either side of the drape to provide a structure corresponding substantially to that shown for main sheet 22 in FIG. 1. Also, it will be understood that main sheet 22 could be rectangular rather than T-shaped. Finally, if desired, flaps of material could be added to the lower edge of cross-arm portion 26 at either side of the drape to provide the armboard flap structure disclosed in U.S. Pat. No. 3,856,006.

As indicated earlier, drape 20 is particularly suited for use in cardio-vascular surgery and is preferably sufficiently long, not only to cover the anesthesia screen and the body of the patient, but also to fall vertically for a distance of about 18 inches or so over the foot of the operating table. By way of example and not limitation, it has been found that drape 20 is suitably about 110 inches to about 152 inches, and preferably about 130 inches in length (i.e., the distance from top edge 27 to bottom edge 28). Also by way of example, body portion 25 of the drape can be from about 60 inches to 84 inches, and preferably about 72 inches, in width (i.e., the distance between side edges 25a and 25b); crossarm portion 26 can be from about 90 inches to about 106 inches, and preferably about 98 inches, in width (i.e., the distance between side edges 26a and 26b). The lengths of body portion 25 and crossarm portion 26, which when added together are approximately equal to the overall length of the drape, can be varied with respect to one another. Suitably, the length (i.e., the distance along side edge 26a) of crossarm portion 26 is from about 30 inches to about 44 inches, and is preferably about 36 inches. The length (i.e., the distance along side edge 25a) of body portion 25 is suitably from about 80 inches to about 108 inches, and preferably is about 94 inches.

As illustrated in FIG. 1 chest fenestration 30 is substantially rectangular in shape and is defined by inner edges 30a, 30b, 30c and 30d of the drape. Fenestrated surgical drapes are well known in the art and it will be understood that fenestration 30 may, according to the particular purpose for which the drape is intended, have an oval, square, circular or other configuration.

Similarly, the size of fenestration 30 may be varied according to the use for which the drape is intended. In drape 20, for use in cardiovascular surgery, fenestration 30 is about 16 inches long and about 9 inches wide. Top edge 30c of fenestration 30 is conveniently located about 39 inches from top edge 27 of the drape, while the sides of the fenestration are conveniently located equidistantly from the sides of the drape. It will be understood that the above dimensions and locations are given by way of example and not by way of limitation.

Surgical drape 20 has a second fenestration 40 which may be conveniently referred to as the leg fenestration. Fenestration 40 is substantially rectangular in configuration and is defined by interior edges 40a, 40b, 40c and 40d, of the drape. As will be seen by reference to FIG. 1, fenestration 40 is wider and longer than fenestration 30. As with chest fenestration 30, leg fenestration 40 may be varied in configuration and dimensions. The width of fenestration 40 may vary from about 16 inches to about 20 inches, with a very suitable width being in the range of about 18 inches. The length of fenestration 40 may conveniently be from about 36 inches to about 40 inches with a length of from about 37 inches to about 39 inches being preferred. The top edge of fenestration 40 may be spaced from about 5 inches to about 7 inches from the bottom edge of fenestration 30, about 6 inches geing quite suitable.

In the embodiment illustrated in the drawings, chest fenestration 30 is substantially rectangular in shape. It will be recognized that this fenestration may vary in both size and shape and, in fact, need not necessarily be four-sided.

Again by way of example and not limitation, it has been found that the chest fenestration in a drape intended particularly for cardiovascular surgery should be about 9 inches wide and about 16 inches long.

Fenestrations 30 and 40 are preferably, but not necessarily, surrounded by a reinforcing panel 50 which provides increased strength along with improved resistance to tearing and abrasion. The reinforcing panel may comprise a second layer of the same material used for main sheet 22 or it may be a different material. Where it is desired, as would usually be the case, to have a reinforced drape, panel 50 preferably comprises a material which has a liquid absorbent upper surface and a liquid impervious lower surface. A liquid absorbent nonwoven fabric 51 suitably laminated, e.g., with an adhesive, to a thin sheet or film 53 of liquid impervious thermoplastic polymer is preferably used for reinforcing panel 50 (see FIGS. 5 and 5a). This reinforcing panel is secured in place, preferably with an adhesive, on the drape so that its film portion is secured to the upper surface of main sheet 22. The liquid absorbent surface of the reinforcing panel is then exposed on the upper surface of the drape where it can quickly absorb liquids such as wound exudate, irrigating fluids, and blood normally used or encountered in surgery.

It will be observed that reinforcing panel 50 is preferably wide enough so that its opposed side edges 50a, 50b lie between the sides of the fenestrations and the side edges of the drape. Similarly, panel 50 is preferably long enough so that its top edge 50c lies between the top edge of fenestration 30 and top edge 27 of the drape, and bottom edge 50d of the fenestration lies between the bottom edge of fenestration 40 and bottom edge 28. The positioning of reinforcing panel is illustrated primarily in FIG. 1; also see FIGS. 6, 7 and 8 where the absorbent layer 51 and the liquid impervious layer 53 which comprise panel 50 are illustrated in cross-section.

It will be recognized that the length and width of reinforcing panel 50 may vary depending, for example, on the overall size of the drape and also on the size desired for the panel itself. In drape 20, reinforcing panel 50 is suitably about 95 inches long and about 34 inches wide. Top edge 50c is suitably located about 11 inches from the top edge of the drape, and bottom edge 50d is located about 20 inches from the bottom edge of the drape. Side edges 50a and 50b are located about 18 − 19 inches from side edges 25a and 25b, respectively, of the drape, i.e., panel 50 is centered widthwise on the drape.

Modern surgery techniques involve the use of certain auxiliary medical or surgical equipment which include thin, elongated, more or less flexible members such as suction tubing and electical wires from electrical cautery devices, monitoring devices, and the like. It is necessary that such tubing and wires be readily available near the operative site. At the same time, however, these items must be arranged and secured so that they do not interfere with the surgical procedure and so that they will not inadvertently move from their desired place on the drape.

Two such retaining means 60 are provided on drape 20 and satisfy the above mentioned criteria. Retaining means 60 comprises a more or less flat, elongated envelope or container of material such as a plastic or nonwoven fabric. This envelope or container of material, seen in crosssection in FIG. 6, is hollow in the sense that electrical wires, for example, may be threaded therethrough and enclosed therein. The retainer means, which is perhaps best thought of as a flattened tube of material reminiscent of a coin wrapper prior to use, is open at both ends thereof. In use, an electric wire or similar element is threaded through the retainer means which then keeps the element secured on the drape and readily available for use when needed.

Retainer means suitable for use with drape 20 may assume several forms and be arranged on the drape in various ways as more particularly set forth in my copending patent application entitled "Surgical Drape Having Improved Retaining Means," filed simultaneously herewith, the teachings of which application are hereby specifically incorporated by reference.

As illustrated in FIGS. 1 and 6, the preferred embodiment under discussion comprises two such retaining means 60, one near each side edge of reinforcing panel 50. The retainer means can be quickly, conveniently, and economically made from the same material which comprises reinforcing panel 50. Thus, referring especially to FIG. 6, it will be recognized that near each side edge of reinforcing panel 50, the nonwoven/film laminate constituting the reinforcing panel has been gathered into looped configurations which run the entire length of panel 50. Although retainer means 60 is shown in FIG. 6 in a nearly "lay-flat" position, it will be recognized that when the material comprising panel 50 is first gathered into its looped configuration, retainer means 60 will be oriented more or less perpendicularly to the plane occupied by the non-looped portions of the panel. This is illustrated in the phantom portion of FIG. 6 where it will be noticed that a cross-section of the aforementioned perpendicular arrangement of the retainer means in relation to the rest of panel 50 is reminiscent of the shape of the Greek letter omega.

At the lower part of the looped portion, a suitable adhesive 55 may be applied to the adjoining portions of impervious film 53 to secure retainer means 60 in its desired configuration. The upper part of the looped portin forms a conduit or channel 68 running lengthwise of the drape and through which tubing and the like may be threaded. It will be understood that it is not strictly necessary, but only desirable for purposes of sound construction, to apply adhesive 55 as aforementioned at the bottom portion of the retaining means; retaining means 60 will retain its loop-shaped configuration without the application of adhesive to its bottom portion once reinforcing panel 50 is secured to the main sheet of the drape.

Referring to FIG. 4, it will be seen that reinforcing panel 50 is affixed to the upper surface of the drape. Stitching could be used for this purpose but, as shown in FIG. 4a, it is preferably to use an adhesive 55 to attach reinforcing panel 50 to upper surface 23 of the drape.

Each of the fenestrations 30 and 40 is covered with a closure member which comprises a relatively thin (e.g., about 1 mil to 4 mils), flexible plastic film. As seen in FIG. 4, fenestration 30 is covered with closure member 70 and fenestration 40 is covered with closure member 71. Preferably the film comprising closure members 70 and 71 is clear so that it can be seen through and antistatic so as to avoid the build-up of hazardous static electric charges. As will be seen, closure members 70 and 71 (which are often referred to as "incise films" in the art) will be adhered to the skin of the patient during the draping procedure. The incise film serves to keep the fenestration in its proper position on the body of the patient. During surgery, the incise film remains in place on the patient and the surgeon makes the required incision(s) directly through this incise film.

Closure members 70 and 71 are made to be somewhat larger than the fenestrations over which they will be placed. During the manufacture of the drape, the under surface of the closure member is coated with a pressure sensitive adhesive 75 (shown as stippling in FIG. 1) which will both adhere to the skin of a patient and serve to keep the closure member in place over the fenestration. Adhesives having such properties are well known in the surgical drape art and do not form part of the present invention. In assembling the drape, the adhesive adjacent the side, top, and bottom edges of each closure member is brought into contact with the upper surface of the drape over the corresponding edges of the fenestration which is being covered so that each closure member is secured and maintained in its proper position.

After closure member 70 is secured on the drape to close off fenestration 30, a major portion of adhesive 75 which was applied to the closure member's under surface is exposed as a continuous layer on the bottom of the drape and within inner edges 30a, 30b, 30c, and 30d defining fenestration 30. Similarly, after closure member 71 is secured over fenestration 40, a major portion of adhesive 75 which was applied to the under surface of closure member 71 is exposed as a continuous layer on the bottom of the drape and within inner edges 40a, 40b, 40c and 40d defining fenestration 40. These portions of adhesive will be used to secure the drape to the patient's chest and legs. Prior to use, in order to preserve the tackiness of the adhesive and to prevent unwanted adhering of the adhesive to other parts of the drape, the above mentioned exposed major portion of adhesive is protected by a releasably adhered cover sheet or release paper. Release papers are well known in the art and may comprise, for example, wax coated paper stock or silicone coated polyolefin film. In order to provide complete protection of the adhesive, the release sheet must be at least as large as the adhesive layer to which it will be adhered. For convenience, the release sheet is somewhat larger than the adhesive area to which it is adhered. Preferably, an end portion the release paper is folded back upon itself to provide a tab which can be readily grasped by a nurse or attendant, thus facilitating removal of the release sheet prior to draping the patient.

Referring now to FIGS. 4 and 4b, it will be seen that release sheet 76 is adhered to adhesive 75 on the under surface of closure member 70. Release sheet 76 is oversized and its upper edge (that is, the edge which is nearer top edge 27 of the drape in FIG. 4) has been folded back upon itself (FIG. 4) to form grasping tab 76a. The bottom edge 76b of release sheet 76 extends beyond the bottom edge of fenestration 30 and lies in more or less loose contact with the under surface of lower body portion 25.

Closure member 71 carries adhesive 75 (not illustrated in FIG. 4) on its exposed under surface and the adhesive is protected by a plurality of separate release sheets 80, 81 and 82 in the same way that adhesive 75 on member 70 is protected by release sheet 76. Each of the release sheets 80, 81 and 82 covers approximately ⅓ of the exposed adhesive on the underside of closure member 71. Each of the release sheets has grasping tabs designated 80a, 81a and 82a, respectively. Each of the release sheets has an upper edge (the edge in FIG. 4 which is nearer top edge 27 of the drape) and a lower edge (the edge in FIG. 4 which is nearer bottom edge 28 of the drape). Tab 80a of release sheet 80 loosely contacts the lower surface of the upper edge portion of release sheet 81; in the same fashion, grasping tab 81a loosely contacts the lower surface of the upper edge portion of release sheet 82. Grasping tab 82a of release sheet 82 loosely contacts the lower surface of lower body portion 25. The top edge portion of release sheet 80 loosely contacts the lower surface of lower body portion 25.

In the preferred embodiment under discussion, three release sheets are used to protect adhesive 75 on the under surface of closure member 71. It will be appreciated that, due to is extended length, it is necessary to fold drape 20 longitudinally (and also transversely) in order to reduce it to a compact unit which can be conveniently packaged and shipped by the manufacturer. It would be possible, of course, to protect the adhesive on closure member 71 by using a single release sheet in place of release sheets 80, 81, and 82, but this would make it somewhat less convenient to unfold the drape and apply the same to the patient. The use of two release sheets on the adhesive of closure member 71 substantially improves the ease and safety with which the folded drape can be applied to the patient. As described above in connection with drape 20, the use of three release sheets is deemed preferable. Four release sheets could be used, or even five, but this is believed to be a less feasible arrangement in that an increasing number of release sheets would have to be handled by the nurse or attendant. Thus, for a drape 20 having the typical dimensions set forth earlier herein, it is believed that it is best to have three release sheets protect the exposed adhesive on the under side of closure member 71. As will be seen later, the use of three separate release sheets greatly facilitates the unfolding of the drape and the application thereof in an aseptic manner to the patient, prior to and during the draping procedure.

Surgical drape 20 is conveniently assembled in accordance with the following procedure. Lower body portion 25 and upper cross-arm portion 26 are cut in the desired size from a suitable flexible, drapable material such as a nonwoven or scrim reinforced tissue. Lower edge 26c of the cross-arm portion is placed over upper edge 25c of the lower body portion, using about an inch overlap, and two pieces of material are secured together with a layer of adhesive 21 to form main sheet 22 (See FIG. 1). A portion of the drape running inwardly from side edge 25a and side edge 25b is left free of adhesive so as to provide for the flap like arrangement illustrated at the left hand side of FIG. 1. If it is desired to provide a reinforced drape, a suitably sized piece of reinforcement material is selected for reinforcing panel 50. The panel is fixed into position on the upper surface of main sheet 22 with any suitable means, an adhesive being particularly preferred. If it is desired to have retaining means 60 formed from the same piece of material as reinforcing panel 50, then the required looped configurations are formed into the reinforcing material prior to its being adhered to the upper surface of main sheet 22. Fenestrations 30 and 40 are then cut, for example, with scissors or an appropriately sized die, through main sheet 22 and reinforcing panel 50 if the latter is being used. Closure members 70 and 71, with pressure sensitive adhesive 75 on their surfaces, are then adhered on the upper surface of the drape so as to cover fenestrations 30 and 40, respectively. Release sheet 76 is adhered to the portion of adhesive 75 on closure member 70 which is exposed between fenestration edges 30a, 30b, 30c, 30d on the under side of the drape. Release sheets 80, 81 and 82 are selected and folded to provide tabs 80a, 81a and 82a, respectively. These release sheets are then arranged on the under surface of the drape in accordance with the arrangement shown in FIG. 4 to protect the portion of adhesive 75 on closure member 71 which is exposed on the under side of the drape between fenestration edges 40a, 40b, 40c, and 40d.

FOLDING OF THE DRAPE

Drapes of the present invention may be folded into a compact unit which facilitates handling during packaging and storage and which permits the drape to be easily, quickly and aseptically applied to the patient prior to surgery.

As used herein a "forward fold" is a fold in which the upper surface is turned toward the upper surface of the drape around a fold line. A "reverse fold" is a fold in which the upper surface of the drape is turned toward the bottom surface of the drape around a fold line. In the drawings, the letter R indicates a reverse fold and the letter F indicates a forward fold. The numbers preceding the letters F and R refer to the order in which the folding is done.

A discussion of the folding of drape 20 will be greatly facilitated by considering that the drape comprises a bottom section, a central section, and an upper section. Referring especially to FIG. 1, drape 20 comprises a bottom section 115, a central section 116, and an upper section 117. Bottom section 115 of the drape comprises that portion which lies between bottom edge 40d of second fenestration 40 and bottom edge 28 of the drape. Central section 116 of drape 20 comprises that portion which lies between upper edge 30c of first fenestration 30 and lower edge 40d of second fenestration 40. For clarity, the bracket indicating central portion 116 has been put near the left hand side of FIG. 1. The uppermost edge of this bracket is positioned in the drawings so as to coincide with an extension 30c' (shown as a series of dots) of upper edge 30c of fenestration 30. Upper section 117 of drape 20 is that portion which lies between upper edge 27 of the drape and upper edge 30c of first fenestration 30. For purposes of clarity, central section 116 will be understood to include lower edge 40d of fenestration 40 and upper edge 30c of fenestration 30. Thus, a fold line which substantially coincides with edge 40d or edge 30c will be a fold line running through said central section.

Drape 20 may be reduced in size in the longitudinal direction by folding bottom section 115 thereof around one or more fold lines which pass transversely through said bottom section. Alternatively, the drape can be reduced in size by folding bottom section 115 around a fold line which conicides with the lower edge of the central section (which is identical with the upper edge of the bottom section); in this case bottom section 115 has no folds but retains its unfolded configuration and overlies at least a portion of central section 116. Thereafter, the drape may be further reduced in size by folding it one or more times around fold lines which pass through central section 116, it being understood that if central section 115 be folded around a transverse fold line which either passes through leg fenestration 40 or coincides with either upper edge 40c or lower edge 40d of said fenestration, such fold must be a forward fold. Finally, to reduce the size of the drape even further in the longitudinal direction, upper section 117 may be folded around the upper edge of central portion 116 to overlie, or be interleaved with, the previously folded portions of the drape. Alternatively, the drape may be further shortened by folding section 117 around one or more fold lines passing transversely thereof.

The preferred folding of drape 20 will now be described with reference to FIGS. 1, 4 and 10–19. FIGS. 1, 4 and 10 show the location of the fold lines for the preferred folding in the longitudinal direction. Drape 20, when folded in the preferred manner about to be described, may be quickly, easily and aseptically applied to the patient in accordance with accepted operating room draping practices. In the preferred embodiment, fold lines passing through central portion 116 of the drape, including those fold lines which substantially coincide with lower edge 40d of second fenestration 40 and upper edge 30c of first fenestration 30, must be forward folds.

It will be understood that in the preferred embodiment under discussion, the fold around a fold line substantially coinciding with edge 40d must be a forward fold in order that the folded bottom section will contact the upper surface of the drape. If a reverse fold is employed, the folded bottom section will be adjacent the under surface of the drape and, when it is time to drape the patient, will interfere with the nurse's ability to remove one or more of release sheet 80, 81 and 82. For the same reason, the folds around fold lines 6F, 7F, and 8F must be forward folds. Use of reverse folds in any of these cases will put folded portions of the drape adjacent the lower surface of the drape, thus making the removal of the release sheets and subsequent application of the drape very difficult.

The first step in folding drape 20 is to fold bottom section 115 a plurality of times in the direction which runs from the bottom edge of the drape toward the top edge of the drape. A simple fan fold, or a modified fan fold can be used for this purpose. Referring to the bottom portion of FIG. 1, a bottommost portion 91 of bottom section 115 is defined by bottom edge 28 of the drape, fold line 1F and portions of side edges 25a, 25b of the drape. Bottommost portion 91 is forward folded, toward the top of the drape, around fold line 1F. Bottom section 115 is thereafter reverse folded around fold line 2R, forward folded around fold line 3F and reverse folded around fold line 4R. It will be understood that the above described folding sequence for the bottom section of the drape is greatly preferred, but not critical; bottom section 115 may be folded in various other ways.

It should be noted that, in the preferred folding, the next fold line, 5F, substantially coincides with lower edge 40d of fenestration 40, which corresponds to the lower edge of central section 116. As indicated earlier, the fold around this line must be a forward fold. The next two fold lines (6F, 7F) pass through the leg fenestration and the folds through these lines must also be forward folds. The next fold line in the preferred embodiment is 8F and the fold around this line must be a forward fold. It will be observed that the fold line 8F passes transversely of the drape between upper edge 40c of leg fenestration 40 and lower edge 30d of chest fenestration 30. It will be observed that fold lines 5F, 6F, 7F, and 8F are located so that second, or leg, fenestration 40 is "divided" into three more or less equal parts.

Continuing now with the description of the folding, a lower portion 118 (i.e., that portion which lies between fold lines 5F and 8F) of section 116 is, in sequence, forward folded around fold line 5F, forward folded around fold line 6F, forward folded around fold line 7F and forward folded around fold line 8F. FIG. 11 is a perspective view of drape 20 after the fold around fold line 6F has been completed. FIG. 12 is a perspective view after the fold around fold line 7F has been completed and FIG. 13 is a perspective view after the fold around fold line 8F has been completed. Cross-sectional views of the drape in FIGS. 11 and 13 are found in FIGS. 15 and 16, respectively. This folding sequence provides a stack A of folds which overlies an upper portion 119 (i.e., that portion between upper edge 30c of fenestration 30 and fold line 8F) of central section 116 and a small portion of upper section 117. It will be observed that, at this stage of the folding, stack A of folds is on the upper surface of the drape and covers chest fenestration 30 and its closure member 70 (See FIG. 13).

The longitudinal folding is completed by folding at least part of upper section 117 from top edge 27 in a direction toward the original center of the drape. Uppermost portion 93 of upper section 117 is foward folded around fold line 9F, reverse folded around fold line 10R, forward folded around fold line 11F, reverse folded around fold line 12R, and forward folded around fold line 13F. This sequence, which is a simple fan folding in which the last fold is a forward fold, provides a stack B of folds which overlies at least a portion of that part of the drape lying between fold lines 8F and 13F. The extensions of cross-arm portion 26 lying beyond sides 25a, 25b of the drape are then forward folded to provide drape 85 of FIG. 14. When the preferred longitudinal folding of the drape is completed, both stack A of folds and stack B of folds overlie at least a portion of that part of the drape lying between fold lines 8F and 13F. In addition, in the preferred fold drape, stack B of folds also overlies a portion of stack A of folds (See FIG. 17). This arrangement of the stack of folds is preferred because it allows the upper section of the drape to be unfolded over the anesthesia screen prior to the application of the rest of the drape to the patient's body. It will be understood nevertheless that, if desired, the drape can easily be folded so that stack A of folds overlies stack B of folds. It will further be observed that, after the preferred folding steps are completed, release sheet 76 (which is located between fold lines 8F and 13F) is centrally located on the bottom surfce of longitudinally folded unit 85. This is very advantageous because, as can be understood by referring to FIG. 20, at the time of draping the patient, the nurse grasps tab 76a and strips off release cover 76. This exposes adhesive 75 on the under surface of closure member 70 covering chest fenestration 30. It is then easy for the nurse to adhere the drape in its proper position on the patient's chest as the first step in the draping procedure.

The preferred manner for transversely folding longitudinally folded drape 85 will now be described with reference to FIGS. 18 and 19. Longitudinally folded drape 85 may be folded from side to side to provide a completely folded, compact drape by using any desired folding sequence. Preferably a modified fan fold is employed. FIG. 19 shows the location of the fold lines for the transverse folding of longitudinally folded drape 85. The drape is folded from one side edge toward the center, then from the other side edge toward the center. Preferably, when the transverse folding is finished, there are provided two stacks of folds whose inner edges are adjacent each other.

The folding of drape 85 is begun by forward folding a portion thereof adjacent right side edge 86 around fold line 1F. Thereafter the drape is forward folded around fold line 2F, reverse folded around fold line 3R, forward folded around fold line 4F, reverse folded around fold line 5R, and forward folded around 6F. This folding sequence provides a first stack of folds C which overlies at least part of the drape lying between fold line 6F and 12F.

The transverse folding of the drape is completed by forward folding a portion thereof adjacent left side edge 87 around fold line 7F. The drape is then forward folded around line 8F, reverse folded around fold line 9R, forward folded around fold line 10F, reverse folded around fold line 11R, and forward folded around fold line 12F. This provides a stack D of folds which also overlies a portion of the drape between fold lines 6F and 12F. As seen in FIG. 19, stacks C and D of folds which are disposed are adjacent each other on the upper surface of completely folded drape. 95. The transverse folds in the completely folded drape 95 are illustrated in schematic cross-section in FIG. 19. The completely folded drape 95 is shown in the hands of nurse 101 in FIG. 20.

APPLICATION OF THE DRAPE TO THE PATIENT

A suitable method for applying drape 20, folded in the manner set forth above, is illustrated in conjunction with FIGS. 20-25.

FIG. 20 shows the completely folded surgical drape 86 lying on a back table with adhesive layer 75 on closure member 70, along with its release covering 76, facing upwardly. A nurse 101 is shown steadying the folded drape with her right hand and peeling off release covering 76 with her left hand.

In FIG. 21 nurse 101 is shown holding folded drape 86 in position over the chest of patient 105 lying on operating table 110. It will be noticed that the release covering has been completely removed and discarded, and that adhsive 75 on closure member 70 is facing the patient's chest. The drape is being held so that upper edge 30c of fenestration 30 is at the top.

In FIG. 22 the closure member 70 has been placed into contact with the patient's chest, the drape has been unfolded from side to side, and (although it cannot be seen in FIG. 22) stack B of folds has been unfolded toward the top of the operating table so that it covers the upper part of the patient's body and the anesthesia screen. Nurse 101 on the left side of the patient and nurse 102 on the right side of the patient are holding stack A of folds (partially unfolded around fold line 8F) and assistant 103 is shown removing section 80 of release material from the drape.

In FIG. 23 the upper portion of closure member 71 has been pressed into contact with the lower abdomen and hip region of the patient, and the drape, still being held by the nurses, has been partially unfolded along line 7F. Assistant 103 is shown pulling section 81 of release material from the drape.

In FIG. 24, the central portion of closure member 71 has been pressed into contact with the knee region of both legs of the patient and the drape has been partially unfolded around fold line 6F. Assistant 103 is shown pulling section 82 of release material from the drape.

FIG. 25 shows the patient completely draped. The bottom portion of closure member 71 has now been pressed into contact with the lower leg and angle portion of the patient's body. Bottom section 116 of the drape has been unfolded toward, and hanges over, the bottom edge of the operating table. Retainer members 60 are in position on the drape and are aligned generally with the side edges of the operating table. Cross-arm portion 26 of the drape is now seen in position over the anesthesia screen. Thus, it will be seen that, after the drape has been applied to the patient in the manner just described, closure member 70 which covers the chest fenestration is adhered to the chest region of the patient. Closure member 71 covering second fenestration 40 has been pressed into contact with the patient's legs in the region of his body extending generally from the waist down to his feet. The drape is secured in its desired position by adhesive layers 75 on the lower surfaces of closure members 70, 71. Advantageously, both legs of the patient are exposed to the surgeon's view through the closure member 71. thus, if it happens that the vein in the first leg selected by the surgeon is unsuitable for use in the subsequent heart surgery, the other leg will be immediately available as a source for the needed vein.

As can be appreciated, due to the fact that the drape was folded in the preferred manner earlier described, the drape can be applied quickly while adhering to generally accepted standards for aseptic draping. During the unfolding, successive portions of closure member 71 are presented in step wise fashion to the draping team. Thus, release sheet 80 is first removed, exposing approximately a third of the total adhesive on the under surface of closure member 71. This portion of adhesive (about ⅓ of the total) is brought into contact with the patient's body without having to be concerned with the problems that arise out of handling large sections of material bearing adhesive. Thereafter, release sheet 81 is removed, exposing another more or less central portion of the adhesive, this section of adhesive also being easy to handle owing to its reduced size. Finally, release sheet 82, which up until this point has protected the lower portion of the adhesive from coming into advertent and unwanted contact with the patient, staff, or other portions of the drape, etc., is removed, exposing the last portion of adhesive. This smoothed into contact with the patient's body, after which the drape is unfolded to overhang the bottom ede of the operating table.

What is claimed is:

1. A surgical drape comprising a main sheet of flexible, drapable material, said main sheet having an upper surface, a lower surface, a top edge, a bottom edge, and a pair of opposed side edges, said main sheet having at least two fenestrations therein, each of said fenestrations being covered on the upper surface of the drape by a closure member comprising a thin, flexible piece of polymeric film having upper and lower surfaces, said closure members having adhered to their exposed lower surfaces a coating of pressure sensitive adhesive, each of said adhesive coatings being protected, prior to use of the drape, by a removably adhered release covering; said main sheet having secured to its upper surface at least one retainer member made from a generally flexible material and comprising an elongated, open-ended conduit through which flexible elements such as suction tubing and the like may be threaded and thereby retained in desired position on the drape.

2. A surgical drape according to claim 1 wherein said main sheet is generally T-shaped in configuration.

3. A surgical drape according to claim 2 wherein said main sheet includes a body portion and a cross-arm portion each having top and bottom edges, the bottom edge of said cross-arm portion being longer than, and attached to, the top edge of said body portion, the top edge of said cross-arm portion and the bottom edge of said body portion comprising the top and bottom edge, respectively, of said main sheet.

4. A surgical drape according to claim 1 which further comprises a reinforcing panel.

5. A surgical drape according to claim 4 wherein at least one of said fenestrations is surrounded by said reinforcing panel.

6. A surgical drape according to claim 5 wherein both of said two fenestrations are surrounded by said reinforcing panel.

7. A surgical drape according to claim 6 wherein said retainer member and said reinforcing panel are formed from a single sheet of material.

8. A surgical drape according to claim 7 wherein said single sheet of material comprises a liquid absorbent upper surface and a liquid repellent lower surface.

9. A surgical drape according to claim 1 wherein said removably adhered release covering protecting the exposed adhesive on the closure member covering said second fenestration comprises a plurality of release sheets.

10. A surgical drape according to claim 9 wherein said removably adhered release covering comprises three said release sheets and each of said release sheets has an end portion thereof folded back upon itself to form a grasping tab.

11. A surgical drape according to claim 1 wherein said generally flexible material comprising said retainer member is selected from the group consisting of a plastic film, a woven fabric, nonwoven fabric, and a liquid absorbent material laminated to a polymeric film.

12. A surgical drape comprising a main sheet of flexible, drapable material, said main sheet having an upper surface, a lower surface, a top edge, a bottom edge, and a pair of opposed side edges; said main sheet having first and second fenestrations therein, each of said fenestrations having a top edge, a bottom edge, and a pair of opposed side edges, said first fenestration being located between the upper edge of said second fenestration and the top edge of said main sheet; each of said fenestrations being covered on the upper surface of the drape by a closure member comprising a thin, flexible piece of polymeric film having upper and lower surfaces, said closure members having adhered to their exposed lower surfaces a coating of pressure sensitive adhesive, each of said adhesive coatings being protected, prior to use of the drape, by a removably adhered release covering; said main sheet having a plurality of transverse fold lines established thereon;

a first of said fold lines substantially coinciding with said lower edge of said second fenestration; a second of said fold lines passing through said second fenestration between said first of said fold lines and said upper edge of said second fenestration;

a third of said fold lines passing through said second fenestration between said second of said fold lines and the upper edge of said second fenestration; a fourth of said fold lines passing through said drape between the upper edge of said second fenestration and the top edge of said main sheet; and a fifth of said fold lines passing through said drape between said fourth fold line and the top edge of said main sheet; that portion of the drape between the bottom edge of the main sheet and said first of said fold lines being preliminarily folded to reduce the size of said portion; said drape thereafter being forward folded, in sequence and toward the top edge of the main sheet, around said first, said second, said third and said fourth fold lines to provide a first stack of folds overlying that portion of the drape between said fourth fold line and said fifth fold line; that portion of the drape between its top edge and said fifth fold line being preliminarily folded to reduce its size and thereafter being forward folded around said fifth fold line to provide a second stack of folds overlying that portion of the drape between said fourth fold line and said fifth fold line.

13. A surgical drape according to claim 12 wherein said fourth fold line substantially coincides with said lower edge of said first fenestration.

14. A surgical drape according to claim 12 wherein said fourth fold line passes through said drape between the upper edge of second fenestration and the lower edge of said first fenestration.

15. A surgical drape according to claim 14 wherein said fifth fold line passes through said drape between the lower edge of said first fenestration and the top edge of said main sheet.

16. A surgical drape according to claim 15 wherein said fifth fold line substantially coincides with the upper edge of said first fenestration.

17. A surgical drape according to claim 15 wherein said fifth fold line passes through said drape between the upper edge of said first fenestration and the top edge of said main sheet, whereby said first fenestration lies between said fourth fold line and said fifth fold lines.

18. A surgical drape according to claim 17 wherein said second and said third fold lines are located so as to divide said second fenestration into three more or less equal portions.

19. A drape according to claim 17 wherein said second stack of folds overlies said first stack of folds.

20. A drape according to claim 17 wherein said removably adhered release covering protecting the exposed adhesive on the closure member covering said second fenestration comprises three release sheets, one of said sheets covering said adhesive in the area between said first fold line and said second fold line; a second of said sheets covering said adhesive in the area between said second fold line and said third fold line; and a third of said sheets covering said adhesive in the area between said third fold line and said fourth fold lines.

21. A drape according to claim 20 wherein each of said three sheets has an end portion thereof folded back upon itself to form a grasping tab.

22. A drape according to claim 21 wherein said release covering protecting the exposed adhesive on the closure member covering said first fenestration has an end portion thereof folded back upon itself to form a grasping tab.

23. A surgical drape comprising a main sheet of flexible, drapable material, said main sheet having an upper surface, a lower surface, a top edge, a bottom edge and a pair of opposed side edges; said main sheet comprising a bottom section, a central section having lower and upper portions, and an upper section; said bottom section being folded a plurality of times toward the top edge of the drape; said central section being forward folded, in sequence and toward the top edge of the drape, a plurality of times whereby there is provided a first stack of folds overlying the upper surface of said upper portion of said central section; said upper section being folded a plurality of times from the top edge of said main sheet toward the previously folded portions of the drape to provide a second stack of folds overlying the upper surface of at least part of said upper portion of said central section.

24. A surgical drape according to claim 23 wherein the last fold in said bottom section is a reverse fold.

25. A surgical drape according to claim 24 wherein said central section is folded at least four times.

26. A surgical drape according to claim 23 wherein said bottom section is folded four times, the first and third folds being forward folds and the second and fourth folds being reverse folds.

27. A surgical drape according to claim 25 wherein said upper section is folded five times, the first, third and fifth folds being forward folds and the second and fourth folds being reverse folds.

28. A surgical drape according to claim 23 in which said central section further comprises at least one fenestration; the last fold in said bottom section being a reverse fold; and said central section being folded at least four times.

29. A surgical drape according to claim 28 wherein said central section comprises a second fenestration.

30. A surgical drape according to claim 29 in which said fenestrations are covered with closure members comprising a thin polymeric film, said closure members having their lower surfaces coated with an adhesive.

31. A surgical drape according to claim 30 further comprising removably adhered release covers on said adhesive.

32. A surgical drape according to claim 28 wherein said main sheet is generally T-shaped in configuration.

* * * * *

UNITED STATES PATENT AND TRADEMARK OFFICE
CERTIFICATE OF CORRECTION

PATENT NO. : 4,027,665  Page 1 of 2

DATED : June 7, 1977

INVENTOR(S) : George W. Scrivens

It is certified that error appears in the above-identified patent and that said Letters Patent are hereby corrected as shown below:

At Column 3, Line 32, "A" should be -- a --.
At Column 3, Lines 46-47, "leg fenestration" should be -- "leg fenestration." --.
At Column 5, Line 64, "electical wires" should be -- electrical wires --.
At Column 6, Line 50, "portin" should be -- portion --.
At Column 6, Line 63, "preferably" should be -- preferable --.
At Column 7, Line 55, after "portion" and before "the", insert -- of --.
At Column 8, Line 25, "to is extended" should be -- to its extended --.
At Column 8, Line 58, after "and" and before "two", insert -- the --.
At Column 9, Line 10, after "their" and before "surfaces", insert -- lower --.
At Column 11, Line 51, "fold" should be -- folded --.
At Column 11, Line 62, "surfce" should be -- surface --.
At Column 12, Line 28, after "around" and before "line", insert -- fold --.
At Column 12, Line 35, ".95." should be -- 95. --.
At Column 13, Lines 4-5, after "along" and before "line", insert -- fold --.
At Column 13, Line 16, "hanges" should be -- hangs --.
At Column 13, Line 32, "thus" should be -- Thus --.
At Column 13, Line 54, "advertent" should be -- inadvertent --.
At Column 13, Line 57, "This smoothed" should be -- This is smoothed --.
At Column 13, Line 59, "ede" should be -- edge --.

UNITED STATES PATENT AND TRADEMARK OFFICE
CERTIFICATE OF CORRECTION

PATENT NO. : 4,027,665

DATED : June 7, 1977

INVENTOR(S) : George W. Scrivens

It is certified that error appears in the above-identified patent and that said Letters Patent are hereby corrected as shown below:

At Column 14, Line 49, after "fabric," and before "nonwoven", insert -- a --.

Signed and Sealed this

Fifteenth Day of May 1979

[SEAL]

Attest:

RUTH C. MASON
Attesting Officer

DONALD W. BANNER
Commissioner of Patents and Trademarks